United States Patent [19]

Kuperstein

[11] Patent Number: 4,461,304

[45] Date of Patent: Jul. 24, 1984

[54] MICROELECTRODE AND ASSEMBLY FOR PARALLEL RECORDING OF NEUROL GROUPS

[75] Inventor: Michael Kuperstein, Cambridge, Mass.

[73] Assignee: Massachusetts Institute of Technology, Cambridge, Mass.

[21] Appl. No.: 91,648

[22] Filed: Nov. 5, 1979

[51] Int. Cl.$^3$ .............................................. A61B 5/04
[52] U.S. Cl. ................................ 128/642; 339/17 F; 339/272 A
[58] Field of Search ............... 128/639, 642, 784, 670; 339/17 F, 66 M, 75 M, 272 A

[56] References Cited

U.S. PATENT DOCUMENTS

| | | | |
|---|---|---|---|
| 3,629,787 | 12/1971 | Wilson et al. | 339/17 F |
| 3,916,877 | 11/1975 | Beckman | 128/670 |
| 4,261,372 | 4/1981 | Hansen et al. | 128/784 |
| 4,284,085 | 8/1981 | Hansen et al. | 128/784 |

OTHER PUBLICATIONS

Mercer, "Design, Fabrication and Testing ... Biostimulation", Technical Report No. 5306-2, pp. 45-73, May 1976, Stan. Elec. Lab.
Leask et al., "A Multi-Pole Printed Circuit Electrode", The Lancet, #7342, May 16, 1964, p. 1082.
Wise et al., "A Low-Capacitane Multielectrode ... ", IEEE Trans on Bio. Eng., vol. 22, No. 3, pp. 212-219, May 1975.
Gross et al., "A New Fixed Array ... System ... ", Neuroscience Letters, 6, 101-105, 1977.
Loeb et al., "Analysis and Microelectronic Design ... ", Med. & Biol. Eng. & Comput., 15, 195-201, 1977.
May et al., "A Tantalum-on-Sapphire Microelectrode Array", IEEE Trans on Electron Devices, vol. ED-26, No. 12, Dec. 1979.
Mercer et al., "Photolithographic ... Microelectrode Arrays ... ", IEEE Trans on Bio. Eng., vol. BME-25, No. 6, Nov. 1978.
Pickard et al., "Printed Circuit Microelectrodes ... ", J. Exp. Biol., 64, 39-44, 1976.
Pickard et al., "Flexible Printed Circuit Probe ... ", Med. & Biol. Eng. & Comp., 17, 261-267, 1979.
Pickard, "Printed Circuit Microelectrodes", Trends in Neurosciences, Oct. 1979.
Pochay et al., "A Multichannel Depth Probe ... ", IEEE Trans on Bio. Eng., vol. BME-26, No. 4, 199-206, Apr. 1979.
Sonn et al., "A Prototype Flexible Microelectrode ... ", Med. & Biol. Eng., 778-790, Nov. 1974.
Thomas et al., "A Miniature Microelectrode Array ... ", Experimental Cell Research, 74, 61-66, 1972.
Wise et al., "An Integrated Circuit . . . Microelectrodes", IEEE Trans on Bio. Eng., vol. BME 17, No. 3, 238-247, Jun. 1979.
Prohaska et al., "A Multielectrode for Intracontical ... ", Electrocephalography & Clin. Neur., 1977, 42:421-422.
Petsche et al., "Simultaneous Laminar . . . Seizures", Electrocephalography & Clinical Neur., 1977, 42:414-416.

Primary Examiner—Lee S. Cohen
Attorney, Agent, or Firm—Arthur A. Smith, Jr.; James M. Smith

[57] ABSTRACT

A multi-microelectrode has a plurality of sensing elements formed in a linear array along a face of a metal foil substrate. The foil substrate is sufficiently rigid and tough to have a very small volume along a needle length yet support the array of sensing elements and their leads. The preferred substrate materials are tungsten and molybdenum. The leads are insulated from the substrate and from the surrounding environment. A multi-microelectrode is supported in a microelectrode assembly by a connector which includes a guide channel on a support plate. Electrical contacts which may be conformable to the microelectrode are located in the guide channel, and the microelectrode is clamped against those contacts.

15 Claims, 11 Drawing Figures

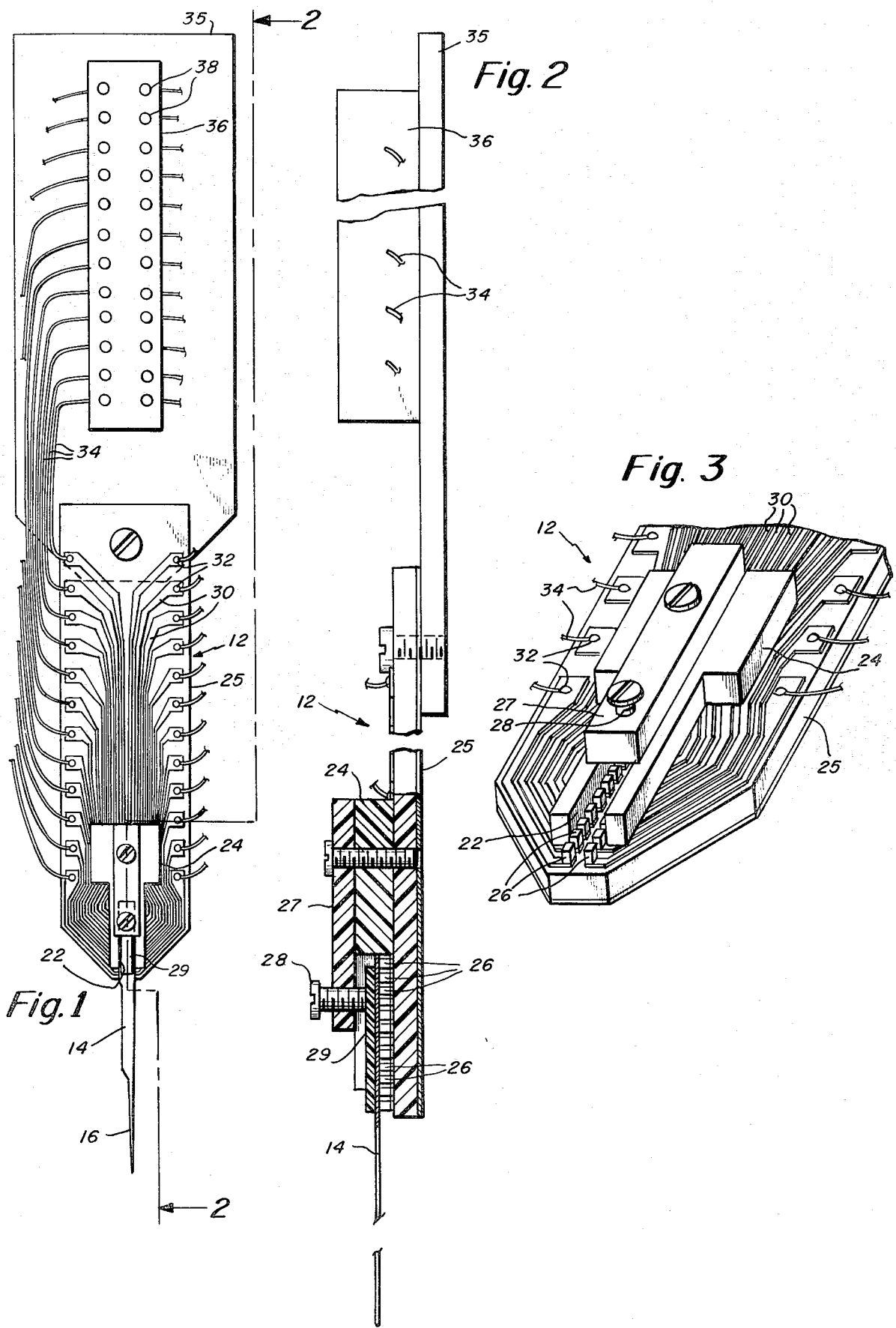

Fig. 7
Fig. 8
Fig. 9
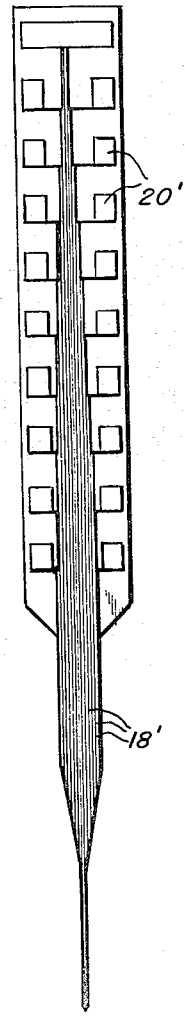
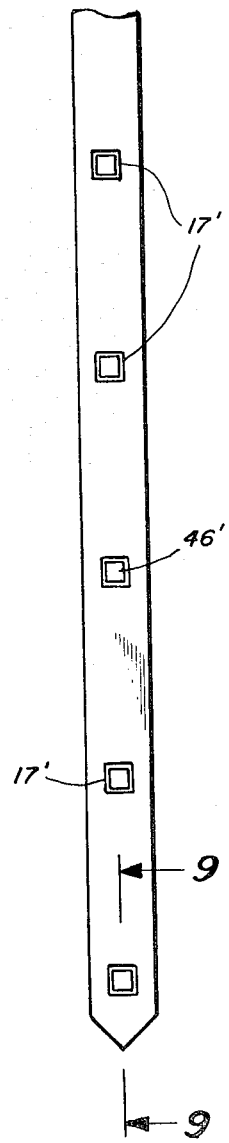
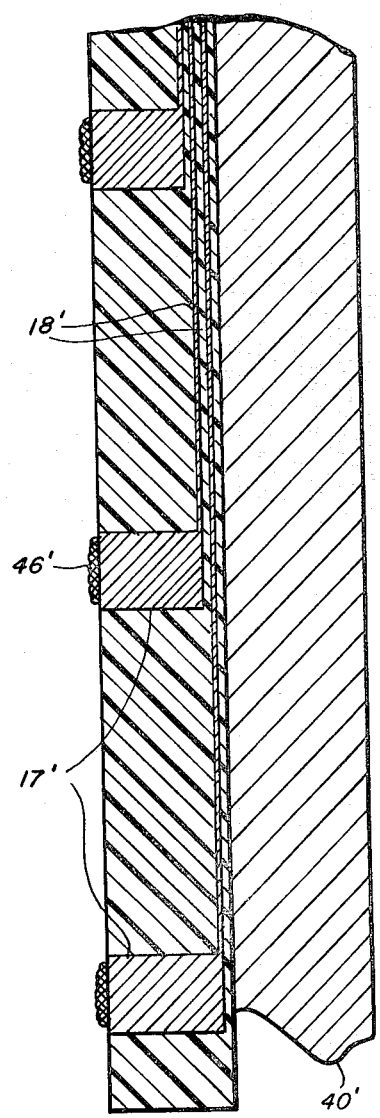

MICROELECTRODE AND ASSEMBLY FOR PARALLEL RECORDING OF NEUROL GROUPS

GOVERNMENT SUPPORT

Work relating to this invention was partially supported by grants from the National Institute of Health: 5 ROI EY00676 and 1 T31 GM07484.

TECHNICAL FIELD

This invention relates to microelectrodes having a plurality of sensing elements and has particular application to the monitoring of the electric potentials of neurons in the brain and of muscles.

BACKGROUND ART

Microelectrodes are major tools in neurophysiological research. By means of very fine electrodes inserted into brain matter the electrical activity generated by neural tissue can be monitored. The microelectrodes most widely used in the field are single strands of insulated metal wire, sharpened and exposed at the tip, or glass micropipettes. These electrodes are only able to sense the electrical activity of single neurons or average activity of a group of neurons at one point. For at least two reasons it is often advantageous to sense multiple neighboring neurons: the work required for each single analysis of neurons within a class is decreased; and data can be gathered on neuronal interactions. Although simultaneous recording from neighboring neurons by separate microelectrodes has been attempted, it is a very difficult procedure.

Multielectrode probes have been suggested by Wise et al. in "An Integrated Circuit Approach To Extracellular Microelectrodes," *IEEE Transactions On Biomedical Engineering*, Vol. BME-17, No. 3, July, 1970, pages 238 to 247, and by Pochay et al. in "A Multichannel Depth Probe Fabricated Using Electron Beam Lithography," *IEEE Transactions On Biomedical Engineering*, Vol. BME-26, No. 4, April 1979, pages 199 through 206. At page 241 of the Wise et al. publication, a probe having three electrodes protruding from its tip is shown. The electrodes are supported by a glass substrate and are coated by electrical insulation. In the more recent Pochay et al. article, three recording sites are formed around the circumference of a glass pipette and are exposed through an upper layer of insulation. The device of the Pochay et al. article has a very small volume along its tip and thus minimizes damage to the brain tissue. However, that device requires the use of a very sophisticated three dimensional fabrication technique and, due to its very thin tip, is subject to breakage during handling.

The quality of data about neuronal group interactions obtained from microelectrodes is directly related to the number of simultaneous recordings made. It would be desirable, for example, to sense the electrical activity of neurons at twenty or more sites through the cortex, the outer layer of the brain. The simultaneous response of neighboring neurons to stimuli would provide a greater insight into the group interaction of neurons.

An object of this invention is to provide a multielectrode probe suitable for sensing the electrical activity of neural tissue at a plurality of sites, the volume of the electrode being small enough to minimize damage to the brain tissue even where as many as 20 sensing sites are provided. A particular object of this invention is to provide such a probe which can be easily handled without breakage and which can be fabricated inexpensively. The increased number of sites increases testing efficiency by increasing the number of cells monitored with each positioning of the microelectrode. Also, parallel recording of neurol groups is possible with a single microelectrode.

DISCLOSURE OF THE INVENTION

A microelectrode embodying the invention includes a plurality of electrical leads formed on a face of an insulated foil substrate. Each lead is terminated by a potential sensing element, also formed on the face of the foil. Each sensing element is exposed through an upper insulating layer. In order to support a large number of sensing elements and their leads with a minimum electrode volume, the foil substrate should be a metal with a Youngs modulus of elasticity of about $30 \times 10^6$ or greater.

Preferably, over 20 sensing sites are spaced in a linear array along the length of a segment of the probe. To minimize damage to the brain tissue, the volume of the segment per site is less than about $3 \times 10^5$ cubic micrometers ($\mu m^3$).

The preferred connector for the microelectrode is a support plate having a guide channel with raised contacts therein. Means are provided for clamping the base portion of the microelectrode against the contacts. A preferred form of contact is a conformable conductive elastomer such as silicon rubber. Individual amplifiers may be provided on the connector plate in a hybrid circuit to provide for a very shortline from the sensing elements to the first amplifier stages.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a view of a microelectrode assembly embodying this invention including a multi-microelectrode mounted to a printed circuit support plate;

FIG. 2 is a longitudinal cross sectional view of the assembly of FIG. 1;

FIG. 3 is a perspective view of the microelectrode support plate of FIGS. 1 and 2;

FIG. 7 is an elevational section of an alternative embodiment of the microelectrode in which the leads to the sensing sites are in stacked layers;

FIG. 8 is a view, greatly enlarged, of the tip of the microelectrode of FIG. 7;

FIG. 9 is a longitudinal cross-sectional view, further enlarged, of three sensing sites at the tip of the microelectrode of FIGS. 7 and 8;

BEST MODE OF CARRYING OUT THE INVENTION

Figure 4:
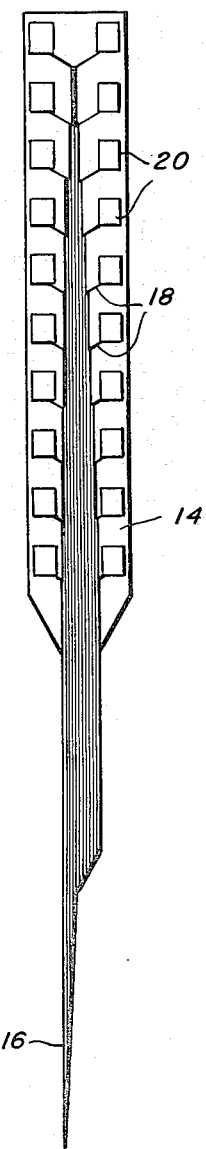
FIG. 4 is an elevational section of the microelectrode in the assembly of FIG. 1, greatly enlarged to show the connecting pads at the connector end thereof.

FIGS. 1 and 2 show a microelectrode assembly suitable for mounting on a microdrive assembly. The microdrive assembly provides precise three dimensional movement of the microelectrode 14 for precise insertion of the electrode into brain matter. As shown in the successively enlarged views of the microelectrode 14 in FIGS. 4, 5 and 6, the needle-like tip 16 of the microelectrode has a plurality of neuron sensing sites 17 along the face thereof. Those recording sites 17 are connected by leads 18 to an equal number of contact pads 20 on the large base of the electrode.

The base of the electrode 14 sits snugly within a channel 22 formed in a U-shaped guide member 24 on a support plate 25. The support plate 25 is shown partially in perspective in FIG. 3. The electrode is pressed against a number of conformable electrical contacts 26 located on the support plate 25 in the guide channel 22. The microelectrode 14 is pressed against the contacts 26 by rectangular metal slab 29. The slab 29 is pressed against the microelectrode by a set screw 28 on a clamping element 27 attached to the guide element 24.

As shown, the contacts are conformable conductive silicon rubber; but other contacts such as spring contacts and solder may also be used. Conformable contact elements have the advantages of conforming to a possibly warped microelectrode and of allowing for large tolerances in fabrication of the contact elements. The contact elements need not be conformable if they are fabricated with a uniform height as, for example, by a high resolution plating technique.

The support plate 25 is a printed circuit board having leads 30 on the board between the contacts 26 and solder beads 32. Wire leads 34, fixed to the solder beads, extend to a socket connector module 36. The module 36 has a socket connector 38 associated with each of the recording sites 17 on the microelectrode 14. The module 36 is mounted to a board 35 which is attached to the microdrive.

Figure 6:
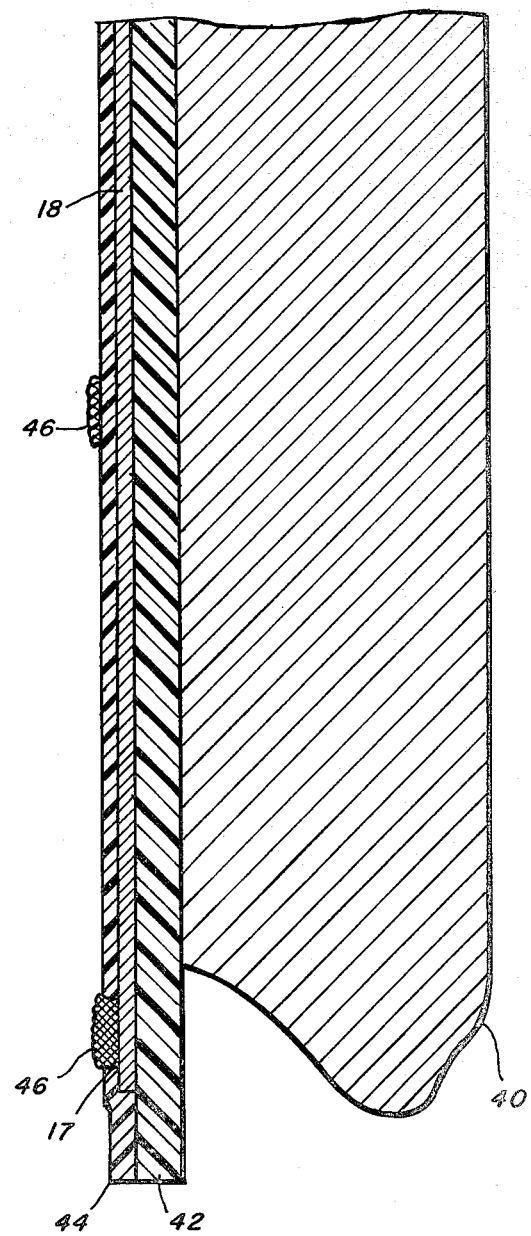
FIG. 6 is a longitudinal cross-sectional view of a single sensing site at the tip of the microelectrode of FIG. 5, greatly enlarge.

As shown in FIG. 6, the microelectrode has a foil substrate 40. The substrate is covered with an insulating layer 42 with less than 5 pf capacitance from each recording site to the foil. On that layer, a pattern of gold leads 18 and recording sites 17 is formed. Another insulating layer 44 is formed over that pattern with the recording sites 17 left exposed. A platinum black capacitance pickup 46 is applied to each site 17 through the openings in the upper layer 44. The platinum black recording sites have a diameter of 12.5 $\mu$m to provide an input capaciticance of 22 pf at 1 KHz. Platinum black has been shown by other researchers to be particularly suitable for use as the capacitive potential sensing elements due to the increased surface area presented by the rough surface and the nature of the chemical boundary layer.

Figure 5:
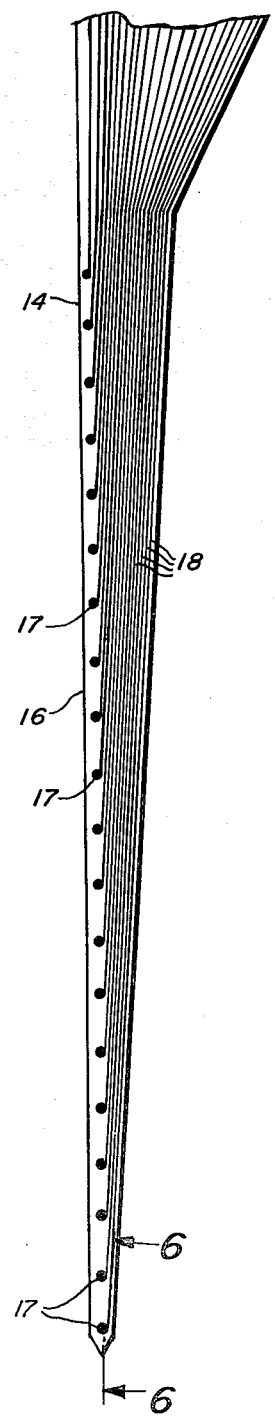
FIG. 5 is a greatly enlarged view of the tip of the microelectrode of FIG. 4 showing the electrical leads to the sensing sites.

The length of the active recording segment of FIG. 5 is 2 mm to accommodate the average thickness of monkey cortex. About twenty recording sites along that 2 mm needle length provide a site density which roughly matches the density of neurons. The sites are spaced 105 $\mu$m apart, whereas neighboring neurons are spaced 20 to 200 $\mu$m apart. The twenty sites are also within the information handling capacities of a computer sampler and analyzer.

With a seventeen micrometer ($\mu$m) thick substrate, a 3 $\mu$m insulating layer 42, a 0.1 $\mu$m thick gold pattern 18, and a 1 $\mu$m insulating layer 44, the device has an overall thickness of about 21 $\mu$m. The width of the needle 16 at the end recording site is 40 $\mu$m and the needle expands to a width of 140 $\mu$m over a 2 mm length. The resultant volume of the needle is thus about $3.7 \times 10^6$ $\mu$m$^3$, or $1.8 \times 10^5$ $\mu$m$^3$ per site. With such a low needle volume per site, many sites provide a large amount of data but the needle is not likely to damage the brain tissue.

To make most efficient use of this invention, at least 15 recording sites should be provided. A somewhat larger needle volume would also be acceptable, but the volume per site for at least 15 sites should not exceed about $3 \times 10^5$ $\mu$m$^3$.

Because conventional microcircuit fabrication techniques are generally planar, the recording sites 17 and leads 18 are formed on the face of a foil substrate 40. The flat substrate enables the microelectrode to be fabricated easily and cheaply using such techniques as photolithography. The planar array of connecting pads at the base of the microelectrode also lends to simple and secure connection to the connector plate. In each of the embodiments shown the recording sites are arranged in a one-dimensional linear array. Other arrays are possible, and a 2 × 12 array has been fabricated.

The dimensions of the substrate 40 are limited by the intended use of the electrode. The microelectrode includes about 20 recording sites spaced along a two millimeter length. To prevent damage to the brain cells, it is important that the volume of the microelectrode along that two millimeter length be minimized. This results in a very thin substrate with a high aspect ratio, the ratio of length to width. With such a low cross-sectional area and high aspect ratio, most possible substrates are either too flexible or too brittle. For example, plastics are very elastic and, if formed as a very thin and narrow substrate, would bend when pushed into brain matter. Ceramics are much more rigid than plastics but tend to be brittle and, with the very high aspect ratio needed to prevent tissue damage along a two millimeter length, would be highly subject to breakage when packaged or handled. Metals, on the other hand, are generally tougher than ceramics and are not as likely to break even at the high aspect ratios required here. A suitable metal foil substrate must further be sufficiently rigid so that it may be readily inserted into the brain matter and so that it is workable during the fabrication technique.

Other requirements for the metal foil substrate are that it be non-toxic and that it be workable using a technique such as photolithography. For photolithography, the substrate must be etchable at a high resolution of plus or minus 12 $\mu$m. A final practical requirement is that the metal foil be fairly inexpensive in order to enable use of large quantities of disposable microelectrodes.

Molybdenum and tungsten have been used as the substrate in microelectrodes shown in FIGS. 4-6. Young's modulus of elasticity for molybdenum is $42 \times 10^6$ psi and Young's modulus for tungsten is $51 \times 10^6$ psi. Both metals are etchable and otherwise suitable for photolithographic techniques. They are non-toxic, and they are fairly inexpensive. Metal substrate having a Young's modulus as low as $30 \times 10^6$ psi are believed suitable for microelectrodes having a recording site length of about two millimeters and having a sufficiently low volume along that length to prevent damage to brain cells.

The following table lists metals having a Young's modulus of at least $30 \times 10^6$ psi along with an indication, where known, as to whether the metal is etchable, toxic, and expensive. The metals are listed in a general order of preference. The first four metals, molybdenum, tungsten, nickel, and stainless steel, are highly preferred. Of those, the high Young's moduli for molybdenum and tungsten make those metals particularly suitable.

| Metal | Young's Modulus $\times 10^6$ psi | Etchable | Toxic | Cost |
|---|---|---|---|---|
| Molybdenum | 42 | yes | no | low |
| Tungsten | 51 | yes | no | low |
| Nickel | 31 | yes | no | low |
| Stainless steel | 30 | yes | no | low |
| Chromium | 36 | yes | — | low |
| Tungsten carbide | 68 | — | no | — |
| Iridium | 75 | — | no | high |
| Rhodium | 42 | — | no | high |
| Ruthenium | 60 | — | no | high |
| Osmium | 80 | — | yes | high |
| Beryllium | 42 | — | yes | moderate |
| Rhenium | 67 | — | — | high |

The microelectrode of FIGS. 4-6 includes all leads in a single layer. In the microelectrode embodiment of FIGS. 7-9, each lead is individually sandwiched between insulating layers. The leads are stacked as shown in FIG. 9. The resultant microelectrode is 40 μm thick, but is only 60 μm wide along its entire length. Thus the volume over a two millimeter length is only $4.8 \times 10^6$ μm$^3$. Twenty-four sites are spaced 82.5 μm apart for a volume per site of $2.0 \times 10^5$ μm$^3$. With this embodiment, relatively wide leads are obtained. Wide leads result in a high fabrication yield per conductive layer. A combination of the two approaches may be used by, for example, providing eight leads in each of three layers.

An object of this invention has been to minimize the volume of the microelectrode even where a large number of recording sites are provided. As stated above, the physical characteristics of the metal foil substrate are instrumental in meeting that object. There are of course minimum limits to the dimensions of the microelectrode even when molybdenum or tungsten are used as the substrates. It has been found that foils of those materials having a thickness of less than 17 μm are not sufficiently workable for use in the fabrication technique described below. Also, the minimum width along the length of the microelectrode, as for example at the tip of the electrode of FIGS. 4-6, must be sufficient to provide a sufficient foil base even after undercutting of the foil during etching. Such undercutting resulting from the foil etching process can be seen in FIGS. 6 and 9. In order for the first insulating layer to adhere properly to the supporting foil substrate, the foil width should be at least 16 μm in the final product. Undercutting of the foil below the insulating layers from each edge is equal to about seven tenths the foil thickness. There being two edges along the length of the microelectrode, the undercutting for the minimum foil thickness of 17 μm is about 24 μm. Add that undercutting to the minimum required foil width and the width of the final microelectrode, that is of the insulating layers, must be at least 40 μm. From the above, given a foil thickness $T_f$, the minimum microelectrode width must be at least $$W_m = 16\mu + 1.4\, T_f$$

If, as in FIGS. 7-9, the microelectrode is not tapered at the tip, the microelectrode width should be even greater to provide an average width of at least about 60 μm along the 2 mm length.

From the socket connector 36 a lead from each site on the multi-microelectrode feeds the signal from each site to a preamplifier having a voltage gain of 25. The outputs from the preamplifiers are then applied through amplifiers, having a gain of 2,000, to signal detectors. Each signal detector includes a Schmitt trigger and flip-flop which provide a high or low output indicative of whether the signal level has gone over a predetermined threshold during a millisecond interval. The detector outputs are multiplexed in a computer interface and are stored as data in the computer. The computer can then provide histogram analysis and a graphic output.

Figure 10:
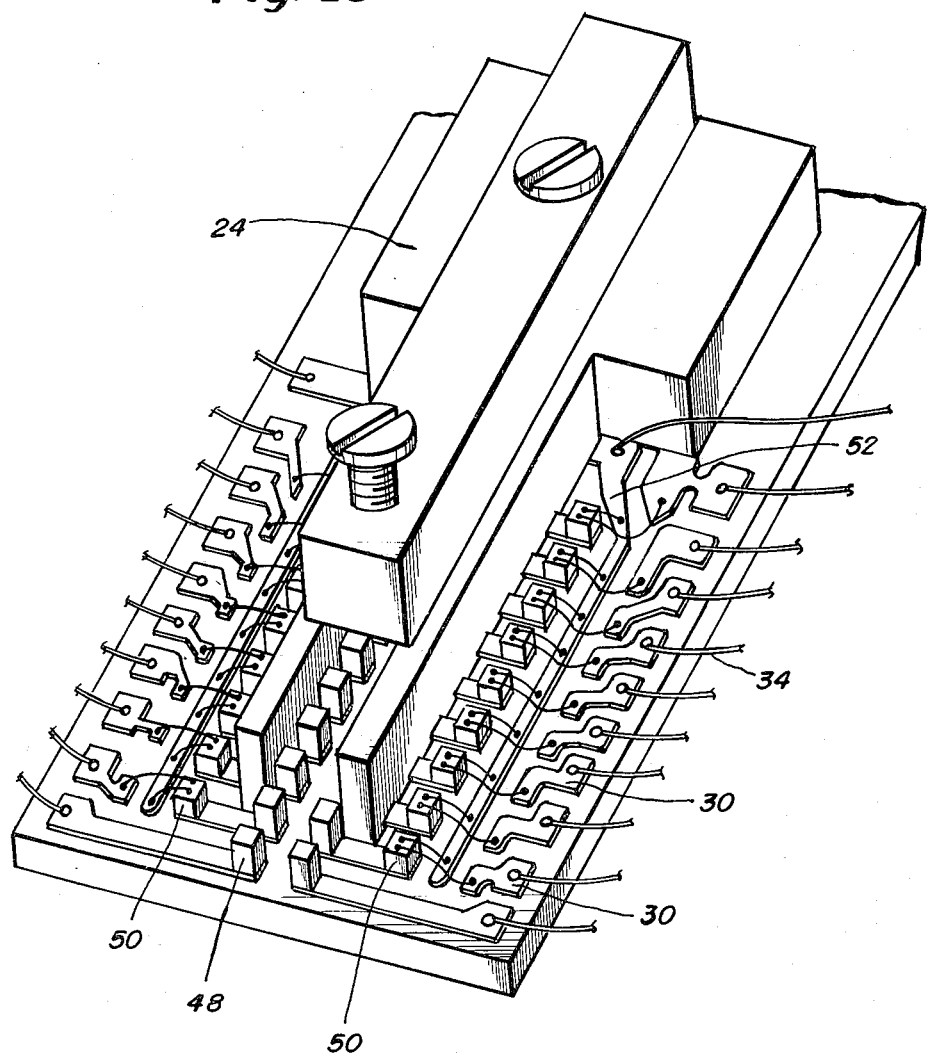
FIG. 10 is a perspective view of a support plate having a hybrid circuit for connection to a microelectrode and for providing first stage amplification.

The above circuit arrangement in which the first stage amplifiers are spaced well away from the recording sites is adequate where the animal is restrained. However, if the animal is allowed to move, the movement results in unacceptable noise levels in the high impedance line between the recording sites and the first amplifier stage. Thus, where the animal is permitted to move, the hybrid circuit of FIG. 10 is included on the printed circuit plate 25. The hybrid circuit includes a number of finger-like contacts 48 on which the deformable contacts 26 can be secured. The contacts 48 lead to field effect transistors 50 which serve as the first stage of amplification and provide high current gain. Printed circuit leads 30 lead from the transistors 50 to the solder beads 32 as before. Power to the FETs is applied through a common power bus 52. Because the hybrid preamplifier has unity voltage gain, the single external amplifier has a voltage gain of 50,000.

Figure 11:
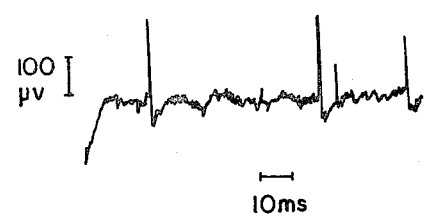
FIG. 11 shows the voltage output with respect to time from one site on the microelectrode.

A typical voltage output from a single recording site 17 is shown in FIG. 11. With a compilation of such outputs, histograms of the electrical activity at many recording sites may be correlated with stimuli. As a result, the response of groups of neurons to stimuli can be studied.

After testing of the animal, the exact positions of all recording sites on the microelectrode can be pinpointed by lesions at the end sites caused by current pulses applied to those sites. These lesions can later be marked by standard histological staining techniques.

Multi-microelectrodes as shown in FIGS. 4-6 which provide multiple outputs have been fabricated by the following method. A flat, bright molybdenum foil of dimensions 1 inch $\times$ 7/8 inch $\times$ 0.0007 inch, is first cleaned in a sulfuric acid and chromic acid glass cleaning solution. It is rinsed in deionized water and baked one-half hour at 200° C. to dry.

The foil is then mounted on a vacuum jig and an HMDS surfactant is spun onto the foil at 6,000 RPM for 15 seconds. A 2:1 mix of KTFR photoresist and thinner is then spun onto the foil at 2,000 RPM for 15 seconds to make the 3 μm insulation layer over the molybdenum foil. The work is then baked at 95° C. for 30 minutes to evaporate the solvent in the KTFR. The photoresist is exposed through a mask outlining ten microelectrodes for 1.5 to 3 minutes at 200 Watts of ultraviolet radiation (W. UV). The exposed photoresist is developed by spraying KTFR developer for one-half minute to provide layers of insulating photoresist in the shapes of the ultimate microelectrodes. The work piece is then rinsed in KTFR rinse and blown dry with nitrogen. It is postbaked at 120° C. for one hour and then at 150° C. for one hour.

A 1,000 Å layer of gold is vapor deposited on the insultating layer and foil. Next, AZ1350B photoresist is spun onto the gold layer at 3,000 RPM for 15 seconds. The photoresist solvent is evaporated by baking the work piece at 95° C. for ten minutes. This spinning and baking of photoresist is repeated. Then the photoresist is exposed to a lead-and-recording-site mask for 4 to 8 seconds at 200 W. UV. The exposed photoresist is developed by immersion in AZ-350 or AZ-351 mixed in a 1:5 mixture with water for 45 seconds. The work piece is rinsed with water and blown dry. The gold thus exposed by removing photoresist is next etched away by immersion in a gold etchant C-35 in a 3:1 mix with water for 9 to 11 seconds. The work piece is rinsed in deionized water and blown dry.

With the gold pattern thus formed, the photoresist over the pattern is removed by immersion in AZ1112A in a 1:2 mix with water for one minute. The work is rinsed and dried and baked at 120° C. for 20 minutes. To provide the upper insulating layer 44, a 1:1 mix of KTFR and thinner is spun onto the work piece at 2,000 RPM for 15 seconds. The work piece is then baked at 95° C. for 20 minutes and exposed to an insulation mask for 30 seconds at 200 W. UV. Photoresist is developed by spraying KTFR developer for one-half minute, followed by a KTFR rinse and blow drying with nitrogen. The work piece is then baked at 120° C. for 20 minutes.

An adhesive tape is applied to the back surface of the foil and the foil, supporting 10 devices, is etched electrolytically in 5% koH, 5% K$_3$Fe(CN)$_6$, and 1% Woolite (trademark) solution. The foil is kept positive and the electrolytic solution is agitated with a spinner. The foil not covered by the photoresist layed in the previous steps is thereby etched away at 200 mA/cm$^2$ to provide 10 separate microelectrodes attached to the adhesive tape.

Each microelectrode is then removed from the tape and placed on a connector plate 25 as shown in FIG. 1. Platinum black is electrolytically plated on the recording sites by passing one microamp through each site with the microelectrode in a solution of 1% PtCl$_3$, 0.01% Pb acetate, and 5% gelatin for 10 seconds.

While the invention has been particularly shown and described with reference to preferred embodiments thereof, it will be understood by those skilled in the art that various changes in form and details may be made therein without departing from the spirit and scope of the invention as defined by the appended claims.

I claim:

1. A microelectrode having a plurality of electrode recording sites suitable for monitoring electrical activity generated by biological tissue in vivo comprising:
   a fine length of insulated foil substrate having a Young's modulus of elasticity of at least $30 \times 10^6$ psi;
   a plurality of electrical leads on a face of the length of insulated substrate, each terminated by a potential sensing element formed on the face of the substrate to form a recording site, at least about 15 potential sensing elements being spaced by less than 200 μm in at least one linear array along a length of the foil substrate of the microelectrode; and
   an upper insulating layer over each lead but not over the terminating potential-sensing element, the volume of the length of the insulated foil substrate supporting the potential sensing elements being less than about $3 \times 10^5$ μm$^3$ per sensing element.

2. A microelectrode as claimed in claim 1 wherein the foil substrate is molybdenum or tungsten or an alloy thereof.

3. A microelectrode as claimed in claim 2 wherein the foil substrate has a thickness $T_f$ of at least about 17 μm, and the minimum width along the length of the microelectrode is at least about $16 \mu m + (1.4 \times T_f)$.

4. A microelectrode as claimed in claim 3 wherein the foil thickness is about 17 μm and the minimum width along the length of the microelectrode is about 40 μm.

5. A microelectrode as claimed in claim 1 wherein the leads to at least some of the potential sensing elements are stacked in separate layers between insulating material.

6. A microelectrode assembly for monitoring electrical activity generated by biological tissue in vivo comprising:
   a connector including a microelectrode guide channel on a support plate, electrical contacts located in the guide channel, and clamping means for clamping a microelectrode in the guide channel against the contacts; and
   a microelectrode clamped in the guide channel by the clamping means including a fine length of insulated foil substrate having a Young's modulus of elasticity of at least $30 \times 10^6$ psi supporting a plurality of electrical leads and potential sensing elements on a face thereof said leads being electrically coupled at one end to said sensing elements and at another end to said contacts, at least about 15 potential sensing elements being spaced by less than 200 μm in at least one linear array along a length of the foil substrate of the microelectrode and the volume of the length of the insulated foil substrate supporting the potential sensing elements being less than about $3 \times 10^5$ μm$^3$ per sensing element.

7. A microelectrode assembly as claimed in claim 6 wherein the foil substrate is molybdenum or tungsten or an alloy thereof.

8. A microelectrode assembly as claimed in claim 6 wehrein the leads to at least some of the potential sensing elements are stacked in separate layers between insulating material.

9. A microelectrode assembly as claimed in claim 6 wherein the contacts are conformable to the microelectrode.

10. A microelectrode connector for supporting and providing electrical connection to a microelectrode which comprises an elongated foil substrate, at least 15 electrode recording sites on the foil substrate, and at least 15 electrical leads extending along the foil substrate from respective recording sites, the connector comprising:
   a support plate;
   a microelectrode guide channel at an end of the support plate, the guide channel being shaped and sized to abut an extended length of the sides of and the end of the base of said microelectrode;
   electrical contacts located in the guide channel and spaced along the length thereof at positions corresponding to the electrical leads on the microelectrode; and
   clamping means for clamping the microelectrode in the guide channel with the microelectrode leads clamped against the contacts.

11. A microelectrode connector as claimed in claim 10 wherein the contacts are conformable to the microelectrode.

12. A microelectrode connector as claimed in claim 11 wherein the conformable electrical contacts are conductive elastomer pads.

13. A microelectrode connector as claimed in claim 12 wherein the elastomer pads are silicon rubber.

14. A microelectrode connector as claimed in claim 10 wherein the support plate is a printed circuit board.

15. A microelectrode connector as claimed in claim 10 wherein the support plate supports a hybrid circuit electrically coupled to said electrical contacts and said hybrid circuit including the first stage of amplification for each electrode recording site.

* * * * *